(12) United States Patent
Fukui et al.

(10) Patent No.: US 6,414,193 B1
(45) Date of Patent: Jul. 2, 2002

(54) PROCESS FOR PRODUCING DIMETHYL SULFOXIDE

(75) Inventors: Yoshiyuki Fukui; Kouji Aburai, both of Shiga; Kosuke Sakamoto, Aichi, all of (JP)

(73) Assignee: Toray Fine Chemicals Co., Ltd. (JP)

( * ) Notice: Subject to any disclaimer, the term of this patent is extended or adjusted under 35 U.S.C. 154(b) by 0 days.

(21) Appl. No.: 09/493,329

(22) Filed: Jan. 28, 2000

(30) Foreign Application Priority Data

Jan. 29, 1999 (JP) .............................. 11-021561

(51) Int. Cl.$^7$ ............................................. C07C 315/02
(52) U.S. Cl. ......................................................... 568/27
(58) Field of Search ............................................ 568/27

(56) References Cited

U.S. PATENT DOCUMENTS

| | | | | |
|---|---|---|---|---|
| 2,581,050 A | * | 1/1952 | Smedslund |
| 2,702,824 A | * | 2/1955 | Wetterholm et al. |
| 2,825,744 A | * | 3/1958 | Smedslund |
| 2,925,442 A | * | 2/1960 | Goheen et al. |
| 2,935,532 A | * | 5/1960 | Hubenett |
| 2,935,533 A | * | 5/1960 | Hubenett |
| 2,938,927 A | * | 5/1960 | Tomlinson |
| 3,045,051 A | * | 7/1962 | Coma |
| 3,647,884 A | * | 3/1972 | Tatsumi et al. |
| 3,708,542 A | * | 1/1973 | Douchet et al. |

OTHER PUBLICATIONS

CA:90:57289 abs JP53096987, Aug. 1978.*
CA:80: 85055 abs of AIChE Symp Ser by Lee et al 69 (134) pp 1–8, 1973.*

* cited by examiner

Primary Examiner—Jean F. Vollano
(74) Attorney, Agent, or Firm—Schnader Harrison Segal & Lewis LLP

(57) ABSTRACT

The present invention provides an efficient dimethyl sulfoxide (DMSO) production process improved in the conversion from dimethyl sulfide (DMS) to DMSO by recycling the NOx used as a catalyst in the continuous oxidation reaction of DMS for producing DMSO, specifically providing a DMSO production process improved in the recovery rate and/or absorption rate of NOx by recovering NOx from the reaction off gas and/or the gas removed from the reaction product solution for re-utilization.

13 Claims, 1 Drawing Sheet

PROCESS FOR PRODUCING DIMETHYL SULFOXIDE

BACKGROUND OF THE INVENTION

The present invention relates to a process for producing dimethyl sulfoxide (hereinafter called DMSO) industrially widely used, for example, as a reaction solvent of medical and agricultural intermediate products, a synthetic reagent or as a special detergent for electronic materials, and the like. In more detail, the present invention relates to an improvement for the process of continuously oxidizing dimethyl sulfide (hereinafter called DMS) using NOx (a mixture of NO, $N_2O_3$, $NO_2$ or $N_2O_4$ or mixture thereof) as a catalyst in a liquid phase for producing DMSO.

PRIOR ART

As a conventional process for producing DMSO, a process of continuously oxidizing DMS using NOx as a catalyst in a liquid phase is publicly known (U.S. Pat. No. 2,825,744 and Japanese Patent Publication (Kokoku) No. Sho 42-9771).

In the DMS oxidizing reaction, NOx gas to be used as a catalyst is supplied together with a gas mainly composed of oxygen to be used as an oxidizing agent to a DMS-containing liquid phase reaction system, and is released outside the reaction system as a reaction off gas, usually to be treated by an alkali for disposal. The amount of NOx gas used is as much as required as a catalyst for DMS. In the oxidation reaction, new NOx is kept supplied as a catalyst to the reaction system, and the used catalyst NOx is disposed of. So, since the conventional process requires a considerable amount of catalyst NOx, the disposal of used catalyst NOx is undesirable in view of cost and effective utilization of a resource.

Furthermore, the amount of oxygen gas used as an oxidizing agent in this process is generally an approximately theoretical amount for liquid phase DMS or slightly larger than it. However, the highly pure oxygen gas with an oxygen concentration of 99% or more used here is high in purchase price, and requires large equipment such as a receiving tank for use of oxygen.

OBJECTS OF THE INVENTION

An object of the present invention is to provide an efficient DMSO production process improved in the conversion from DMS to DMSO in the continuous oxidation reaction of DMS for producing DMSO by recycling NOx used as a catalyst, in order to improve the disadvantage of having to dispose of the used catalyst in the prior art. More specifically, it is an object to provide a DMSO production process improved in the recovery rate and/or absorption rate of NOx by recovering NOx from the reaction off gas and/or the gas removed from the reaction product solution, in the reaction to continuously oxidize DMS by a gas mainly composed of oxygen, using NOx as a catalyst in a liquid phase for producing DMSO.

Another object of the present invention is to provide a low-cost DMSO production process allowing the use of simpler production equipment, by using relatively low pure oxygen gas obtained by the pressure swing adsorption treatment of air.

Other objects of the present invention will be apparent from the following description.

BRIEF DESCRIPTION OF THE INVENTION

The inventors studied intensively to solve the above problems and, as a result, found that dimethyl sulfoxide (DMSO) can be produced very efficiently at a high yield, by supplying at least partially the reaction product solution containing dimethyl sulfoxide (DMSO) and NOx obtained by oxidation reaction of dimethyl sulfide (DMS) to said oxidation reaction for recycling.

The process for producing dimethyl sulfoxide of the present invention, in which dimethyl sulfide is continuously oxidized by a gas mainly composed of oxygen using NOx as a catalyst in a liquid phase, comprises the step of supplying at least partially the reaction product solution containing dimethyl sulfoxide and NOx obtained by said oxidation reaction, to the oxidation reaction for recycling. More specifically, the present invention relates to a process for producing dimethyl sulfoxide, in which dimethyl sulfide is continuously oxidized by a gas mainly composed of oxygen using NOx as a catalyst in a liquid phase using an oxidation reactor, comprising the steps of causing the dimethyl sulfoxide solution to absorb the NOx contained in the reaction off gas in an absorbing column, and supplying the NOx-containing solution to the oxidation reactor for recycling. It is preferable to use the oxygen gas obtained by the pressure swing adsorption treatment of air described later, as the gas mainly composed of oxygen.

The DMSO production process of the present invention also includes the following preferred embodiments.

(1) Nitrogen gas is blown into the reaction product solution at a temperature higher than the reaction temperature, for bringing nitrogen into contact with the reaction product solution, to remove NOx from the reaction product solution mainly composed of NOx and DMSO.

(2) Reaction off gas and/or the gas mainly composed of NOx removed from the reaction product solution is sent to a NOx absorbing column, for recovering NOx.

(3) The reaction product solution remaining after removing NOx is used as the NOx absorbable solution.

(4) NO in the reaction off gas and/or the gas removed from the reaction product solution is oxidized into $NO_2$ which is then sent to a NOx absorbing column, for recovering NOx.

(5) A gas with an oxygen concentration of about 80 to about 96% obtained by pressure swing adsorption treatment is used.

BRIEF DESCRIPTION OF THE DRAWING

The drawing show the outline of the recovering apparatus used for recovery of NOx in the present invention.

DETAILED DESCRIPTION OF THE INVENTION

Figure 1:
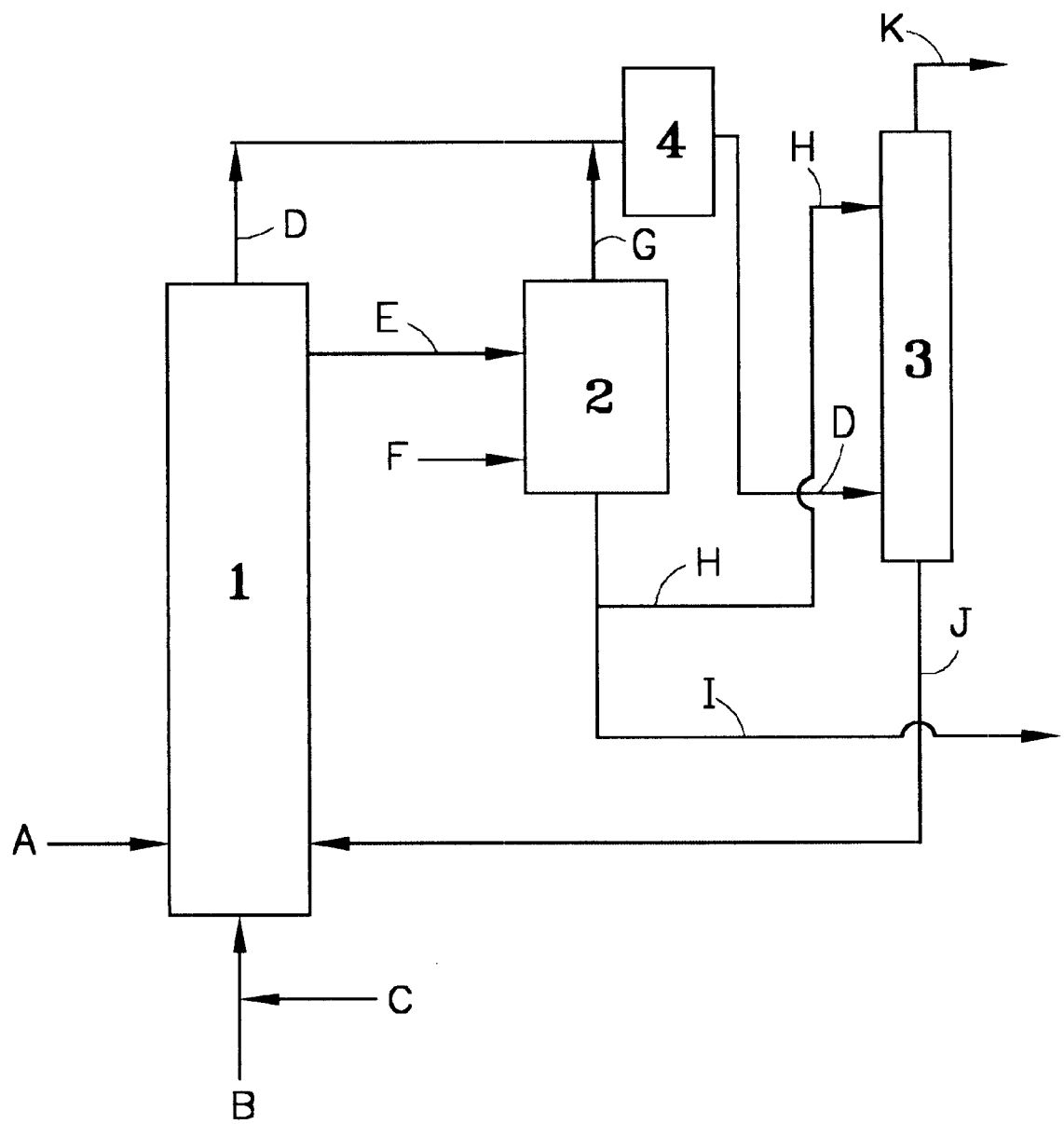

The present invention is described below in more detail.

The present invention relates to an improvement of the process for continuously oxidizing DMS by a gas mainly composed of oxygen using NOx as a catalyst in a liquid phase for producing DMSO. The present invention includes several preferable conditions as described below for improving the conversion from DMS to DMSO in oxidation reaction, and for improving the recovery rate and/or absorption rate of NOx used as a catalyst, and also for allowing the use of a low pure oxygen gas as an oxidizing agent.

The oxidation reaction of DMS in the present invention is exothermic. So, though various types of oxidation reactors are available for the oxidation reaction of DMS, a highly effective mixing reactor and a multitubular reactor can be preferably used. Especially a highly effective mixing reactor can be preferably used.

In the present invention, it is preferable that the temperature in the oxidation reactor is about 10° C. to about 50° C. A more preferable range is about 20° C. to about 40° C. If the temperature is lower than about 10° C. the produced DMSO tends to be coagulated, thereby not allowing the reaction to continue. If higher than about 50° C. dimethyl sulfone (hereinafter called $DMSO_2$) produced by further oxidizing DMSO is produced as a byproduct in a large amount.

It is preferable that the pressure in the reactor during the oxidation reaction is around atmospheric pressure, but the reaction can take place even at a higher pressure.

It is preferable that the catalyst NOx concentration used in the DMS oxidizing reaction in the present invention is about 0.01 to about 0.2 as NOx/DMS ratio by weight. A more preferable range is about 0.05 to about 0.12 as the NOx/DMS ratio by weight. If the reaction is effected at a NOx/DMS ratio by weight of lower than about 0.01, the conversion into DMSO declines disadvantageously. If the reaction is effected at a NOx/DMS ratio by weight of higher than about 0.2, $DMSO_2$ tends to be produced in a large amount.

Furthermore, in the present invention, it is preferable that the oxygen concentration of the gas mainly composed of oxygen (oxygen gas) used as an oxidizing agent is about 80 wt % or more. If a gas with an oxygen concentration of lower than about 80 wt % is used as an oxidizing agent, the conversion into DMSO tends to decline. To keep the conversion high, the reaction solution is retained for a period of time corresponding to more than twice that of an ordinary case.

As the oxygen gas, a highly pure oxygen gas with an oxygen concentration of about 99 wt % or more can also be used, but in the present invention, a relatively low pure oxygen gas obtained by pressure swing adsorption treatment (hereinafter called "the PSA process") can also be used.

The PSA process refers to a method of enhancing the oxygen concentration in a gas by using the difference between oxygen and nitrogen in adsorbing power when the gas is adsorbed by an adsorbent with the rise of pressure and desorbed with the lowering of pressure. As the adsorbent, mainly zeolite is used. In this PSA process, the oxygen concentration in the gas obtained with air as the raw material can be freely adjusted in a range from about 21 wt % to about 96 wt %. In the present invention, an oxygen gas with an oxygen concentration of about 80 wt % to about 96 wt % obtained by treating air by the PSA process can be used.

In the present invention, for efficient oxidation of DMS, it is preferable that the amount of the oxygen gas supplied to the oxidation reaction system is more than the theoretical amount, and the extra unreactive oxygen gas is released outside the reaction system as a reaction off gas together with NOx used as a catalyst. In this case, the NO concentration in the NOx in the reaction off gas is usually about 5 wt % to about 60 wt %, though depending on the process conditions.

The oxygen concentration in the reaction off gas is usually about 10 wt % to about 50 wt %, though also depending on the reaction conditions. It is preferable that the oxygen gas is supplied into the oxidation reactor by an amount slightly larger than the theoretical amount as described above, and it is preferable that the oxygen concentration in the reaction off gas is about 20 wt % or more.

Moreover, to raise the NOx absorption efficiency in the present invention, it is preferable that NO in the reaction off gas is oxidized into $NO_2$ in the gas phase NO oxidizing reactor by oxygen in the mixed gas consisting of NOx and oxygen released outside the liquid phase reactor. Furthermore, in the present invention, to raise the NO oxidation efficiency, it is preferable that a cooler is attached between liquid phase reactor and NO oxidizing reactor. Preferable temperature in the NO oxidizing reactor is lower than about 50° C. A more preferable temperature is lower than about 30° C. So, though various types of reactors are available for the oxidation reaction of NO, a tubular reactor is preferred. It is preferable that the pressure in the reactor during the oxidation reaction is atmospheric pressure, but the reaction can take place even at a higher pressure. Preferable NO concentration in the NOx is less than about 5 wt %. So, it is preferable that the oxygen concentration in the reaction off gas is about 20 wt % or more. If the oxygen concentration in the reaction off gas is lower than about 20 wt %, the NO oxidation efficiency declines.

In the present invention, in the reaction product solution mainly composed of DMSO delivered from the oxidation reactor, the NOx which has not been released as the reaction off gas is dissolved by an amount corresponding to the solubility of NOx in DMSO. In the present invention, the dissolved NOx is removed from the reaction product solution mainly composed of DMSO, by blowing nitrogen gas into the reaction product solution. In this case, the preferable temperature of the reaction product solution into which nitrogen gas is blown is about 40° C. to about 90° C. A more preferable range is about 50° C. to about 80° C. It is preferable that the amount of the nitrogen to be blown in is about 1 wt % to about 7 wt % based on the weight of the reaction product solution. A more preferable range is about 2 wt % to about 6 wt %.

Furthermore, in the present invention, the reaction off gas and/or the gas removed from the reaction product solution respectively containing NOx is passed through a NOx absorbing column, using the reaction product solution remaining after removing NOx as a NOx absorbable solution, to recover NOx from the reaction off gas and/or the gas removed from the reaction product solution.

The absorption efficiency is not so greatly affected by the type of the NOx absorbing column, but a packed column, plate column or wetted wall column can be preferably used.

It is preferable that the amount of the reaction product solution mainly composed of DMSO remaining after removing NOx used as the absorbing solution of the absorbing column is about 5 times or more than the amount of NOx. It is more preferable that the amount is up to about 10 times or more.

EXAMPLES

The present invention is described below more concretely in reference to examples, but is not limited thereto or thereby.

Example 1

The drawing illustrates the outline of the recovery equipment and process used for recovering NOx of the present invention.

In the drawing, DMS was supplied from a pipe 1 at a rate of 100 g per hour (hereinafter expressed as (g/h)), catalyst NOx, from a pipe 2 at a rate of 0.6 (g/h), and oxygen, from a pipe 3 at a rate of 30.5 (g/h), respectively, to an oxidation reactor 4 (4 cm dia. ×50 cm), and oxidation reaction was effected at a reactor temperature of 30° C. The reaction off gas containing oxygen and NOx was supplied through a pipe 5 to a NO oxidizing reactor 6 and a NOx absorbing column 7 (1 cm dia.×50 cm) for recovery of NOx. To a degassing tank 8 (2 cm dia.×20 cm), the reaction product solution produced in the oxidation reactor 4 was supplied from a pipe 9, and furthermore nitrogen gas was supplied from a pipe 10 at a rate of 10 (g/h), to remove NOx in the reaction product solution. The temperature of the degassing tank 8 was 50° C. The NOx removed from the reaction product solution was supplied into the NO oxidizing reactor 6 and the NOx absorbing column 7 through pipes 11 and 5. Furthermore, the reaction solution product mainly composed of DMSO from a pipe 12 was supplied into the NOx absorbing column 7 as a NOx absorbable solution. The amount of the reaction product solution supplied in this case was 50.6 (g/h). The reaction product solution not supplied as the NOx absorbable solution to the NOx absorbing column 7 was supplied to the subsequent step from a pipe 13.

As described above, to the NOx absorbing column 3, the NOx absorbable solution was supplied from the pipe 13 to an upper portion of the absorbing column, and the catalyst NOx was supplied from the pipe 5 to a lower portion of the absorbing column, to let the reaction product solution absorb NOx in the NOx absorbing column 7. The temperature in the NOx absorbing column 7 in this case was 20° C. The oxygen and nitrogen supplied to the NOx absorbing column 7 together with the catalyst NOx from the pipe 5 were released from the top of the NOx absorbing column 7 through a pipe 15 as an off gas. The amounts of oxygen and nitrogen released in this case were 12.2 (g/h) and 10 (g/h), respectively.

The NOx-containing solution released from the NOx absorbing column was recycled from a pipe 14 into the oxidation reactor 4. The amount of the NOx absorbed in this case was 51 (g/h), and the amount of $NO_2$ in the NOx-containing solution was 5.6 (g/h). As a result of the recycling of the NOx absorbable solution, continuous operation could be executed by supplying the catalyst $NO_2$ by 0.6 (g/h) which corresponded to about one tenth of the otherwise required amount.

Example 2

In the drawing, DMS was supplied from the pipe 1 at a rate of 100 (g/h), catalyst NOx, from the pipe 2 at a rate of 6.2 (g/h) and a gas with an oxygen concentration of 90% obtained by PSA, from the pipe 3 at a rate of 34.0 (g/h), respectively to the oxidation reactor 4, and oxidation reaction was effected at a reactor temperature of 30° C. The reaction product solution mainly composed of DMSO produced in the oxidation reactor 1 was supplied from the pipe 9 to the subsequent step. The amount of the reaction product solution supplied in this case was 124.8 (g/h). Furthermore, the reaction off gas containing oxygen and NOx was supplied from the pipe 5 to the subsequent step. The amounts of oxygen and NOx in the reaction off gas in this case were 12.2 (g/h) and 2.4 (g/h) respectively. The conversion into DMSO in this DMS liquid phase continuous oxidation was more than 99%.

Example 3

In the drawing, DMS was supplied from the pipe 1 at a rate of 100 (g/h), catalyst NOx, from the pipe 2 at a rate of 0.6 (g/h) and a gas with an oxygen concentration of 90% obtained by PSA, from the pipe 3 at a rate of 34.0 (g/h), respectively to the oxidation reactor 4, and oxidation reaction was effected at a reactor temperature of 30° C. The reaction off gas containing oxygen and NOx was supplied through the pipe 5 to the NO oxidizing reactor 6 and the NOx absorbing column 7 for recovery of NOx. The reaction product solution produced in the oxidation reactor 4 was supplied from the pipe 9 to the degassing tank 8 at a rate of 124.5 (g/h), and furthermore nitrogen gas was supplied to the degassing tank 2 from the pipe F at a rate of 10 (g/h), to remove NOx in the reaction product solution. The temperature of the degassing tank 2 in this case was 50° C. The removed NOx was supplied to the NO oxidizing reactor 6 and the NOx absorbing column 7 through the pipes 11 and 5. Furthermore, the reaction product solution mainly composed of DMSO was supplied from the pipe H to the NOx absorbing column 3 as a NOx absorbable solution. The amount of the reaction product solution supplied in this case was 50.9 (g/h). The reaction product solution which was not supplied to the NOx absorbing column as the NOx absorbable solution was supplied to the subsequent step from the pipe 13.

As described above, to the NOx absorbing column 7, the NOx absorbable solution from the pipe 12 was supplied to an upper portion of the absorbing column and the catalyst NOx was supplied to a lower portion of the absorbing column from the pipe 5, to let the reaction product solution absorb NOx. The temperature in the NOx absorbing column in this case was 20° C. The oxygen and nitrogen supplied with the catalyst NOx to the NOx absorbing column 7 from the pipe 5 were released as the off gas from the top of the absorbing column through the pipe 15. The amounts of oxygen and nitrogen released in this case were 11.9 (g/h) and 10 (g/h), respectively.

The NOx-containing solution released from the NOx absorbing column was recycled into the oxidation reactor 4 through the pipe 14. The amount of the NOx-containing solution in this case was 51 (g/h), and the amount of $NO_2$ in the NOx-containing solution was 5.6 (g/h). As a result of the recycling of the NOx-containing solution, continuous operation could be effected by supplying the catalyst NOx by 0.6 (g/h) which corresponded to about one tenth of the otherwise required amount. The conversion into DMSO in this case was 99%.

According to the present invention, since catalyst NOx is recycled for use, the amount of the alkali used as a treating solution can be decreased. Furthermore, since NOx leaks less into the atmosphere, the resource can be effectively used and an environmental problem can be solved, compared to the conventional process. Furthermore, the intended DMSO can be produced at a low cost.

That is, according to the present invention, in the continuous oxidation reaction of DMS for producing DMSO, the NOx used as a catalyst is recycled for use, to improve the conversion from DMS into DMSO, thus allowing efficient production of DMSO. The NOx recovered from the reaction off gas and/or the gas removed from the reaction product solution is re-used, to improve the recovery rate and/or absorption rate of NOx.

Thus, the present invention allows industrially advantageous production of DMSO which is widely used as a reaction solvent for medical and agricultural intermediate products, a synthetic reagent, a special detergent for electronic materials, and the like, or as a solvent of resins, films and fibers.

Furthermore, the present invention allows the production of DMSO at a low cost using simplified equipment, by using a relatively low pure oxygen gas obtained by the pressure swing adsorption treatment of air as an oxidizing agent.

What is claimed is:

1. A process for producing dimethyl sulfoxide comprising:

continuously oxidizing dimethyl sulfide in an oxidation reaction by a gas mainly composed of oxygen using NOx as a catalyst in a liquid phase, at least partially supplying a reaction product solution containing dimethyl sulfoxide and $NO_x$ obtained from said oxidation reaction to the oxidation reaction for recycling, and using oxygen gas obtained by pressure swing absorption treatment of air as the gas mainly composed of oxygen, wherein said oxygen is supplied to said oxidation reaction in an amount greater than the theoretical amount based on dimethylsulfide content.

2. A process for producing dimethyl sulfoxide comprising:

continuously oxidizing dimethyl sulfide in an oxidation reaction by a gas mainly composed of oxygen using NOx as a catalyst in a liquid phase, at least partially conducting the reaction product solution containing dimethyl sulfoxide and NOx obtained by said oxidation reaction to the oxidation reaction for recycling, causing dimethyl sulfoxide solution to absorb NOx contained in a reaction off gas in an absorbing column, and supplying the NOx-containing solution to the oxidation reactor for recycling, wherein nitrogen gas contacts the reaction product solution at a temperature higher than the oxidation reaction temperature to remove NOx from the reaction product solution mainly composed of dimethyl sulfoxide.

3. A process for producing dimethyl sulfoxide comprising:

continuously oxidizing dimethyl sulfide in an oxidation reaction by a gas mainly composed of oxygen using NOx as a catalyst in a liquid phase, using oxygen gas obtained by the pressure swing adsorption treatment of air as the gas mainly composed of oxygen, at least partially conducting the reaction product solution containing dimethyl sulfoxide and NOx obtained by said oxidation reaction to the oxidation reaction for recycling, causing dimethyl sulfoxide solution to absorb NOx contained in a reaction off gas in an absorbing column, and supplying the NOx-containing solution to the oxidation reactor for recycling, wherein nitrogen gas contacts the reaction product solution at a temperature higher than the oxidation reaction temperature to remove NOx from the reaction product solution mainly composed of dimethyl sulfoxide.

4. The process defined in claim 2, wherein nitrogen gas is contacted with the reaction product solution at a temperature above the oxidation reaction temperature, in the range of about 40–90° C. to remove NOx from said reaction product.

5. The process defined in claim 4, wherein said temperature is about 50–80° C.

6. The process defined in claim 5, wherein the content of said nitrogen gas is about 1–7 wt % of the reaction product solution.

7. The process defined in claim 6, wherein said percentage is about 2–6 wt %.

8. The process defined in claim 2, wherein NO in the resulting off gas is oxidized to NOx in an oxidizing reactor, and the NOx is absorbed, and wherein the temperature of said oxidizing reactor is less than about 50° C.

9. The process defined in claim 8, wherein the pressure of said oxidizing reactor is at least atmospheric.

10. The process defined in claim 2, wherein the catalyst concentration in the oxidation reaction is in the ratio of about 0.01–0.2 NOx/dimethyl sulfide.

11. The process defined in claim 10, wherein said ratio is about 0.05–0.12 NOx/dimethyl sulfide.

12. The process defined in claim 2, wherein said oxidation reaction temperature is about 10–50° C.

13. The process defined in claim 12, wherein said temperature is about 20–40° C.

* * * * *

UNITED STATES PATENT AND TRADEMARK OFFICE
CERTIFICATE OF CORRECTION

PATENT NO.    : 6,414,193 B1
DATED         : July 2, 2002
INVENTOR(S)   : Fukui et al.

It is certified that error appears in the above-identified patent and that said Letters Patent is hereby corrected as shown below:

Column 2,
Line 3, please delete "(DMSO)"; and
Line 47, please change "show" to -- shows --.

Column 5,
Line 18, please change "column 3" to -- column 7 --; and
Line 19, please change "13" to -- 12 --.

Column 6,
Line 8, please change "tank 2" to -- tank 8 --.

Signed and Sealed this

Twenty-sixth Day of November, 2002

Attest:

JAMES E. ROGAN
Attesting Officer    Director of the United States Patent and Trademark Office